(12) United States Patent
Wu et al.

(10) Patent No.: US 11,739,336 B2
(45) Date of Patent: Aug. 29, 2023

(54) PHYTASE MUTANTS

(71) Applicant: Qingdao Vland Biotech Group Co., Ltd., Qingdao (CN)

(72) Inventors: Xiuxiu Wu, Qingdao (CN); Huaming Wang, Qiangdao (CN)

(73) Assignee: Qingdao Vland Biotech Group Co., Ltd., Qingdao (CN)

( * ) Notice: Subject to any disclaimer, the term of this patent is extended or adjusted under 35 U.S.C. 154(b) by 194 days.

(21) Appl. No.: 17/387,909

(22) Filed: Jul. 28, 2021

(65) Prior Publication Data

US 2022/0025384 A1 Jan. 27, 2022

Related U.S. Application Data

(62) Division of application No. 15/524,390, filed as application No. PCT/CN2014/093218 on Dec. 8, 2014, now Pat. No. 11,104,908.

(30) Foreign Application Priority Data

Nov. 21, 2014 (CN) .......................... 201410677220.8
Dec. 8, 2014 (WO) ................ PCT/CN2014/093278

(51) Int. Cl.
  *C12N 15/70*   (2006.01)
  *C12N 9/16*    (2006.01)
  *C07K 14/47*   (2006.01)
  *C07K 14/705*  (2006.01)
  *C12N 15/81*   (2006.01)

(52) U.S. Cl.
  CPC .............. *C12N 15/70* (2013.01); *C12N 9/16* (2013.01); *C12Y 301/02006* (2013.01); *C12Y 301/03008* (2013.01)

(58) Field of Classification Search
  None
  See application file for complete search history.

(56) References Cited

FOREIGN PATENT DOCUMENTS

| CN | 101080491 A | 11/2007 |
|----|-------------|---------|
| CN | 100594239 C | 3/2010  |
| CN | 102002487 A | 4/2011  |
| CN | 102392002 A | 3/2012  |
| CN | 102559632 A | 7/2012  |
| CN | 102943083 A | 2/2013  |

*Primary Examiner* — Suzanne M Noakes
*Assistant Examiner* — Jae W Lee
(74) *Attorney, Agent, or Firm* — Kilpatrick Townsend & Stockton LLP

(57) ABSTRACT

Provided are mutants PHY1, PHY4 and PHY5 of a wild-type phytase APPA. After being treated for 10 min at 80° C., the residual enzyme activities of the mutants PHY1, PHY4 and PHY5 are respectively higher by 33.85%, 53.11% and 75.86% compared with that of APPA-M; after being treated for 5 min at 85° C., the residual enzyme activities of the mutants PHY1, PHY4 and PHY5 are respectively higher by 14.89%, 28.45% and 44.94% compared with that of APPA-M, and the heat resistance of these mutants is significantly higher than that of APPA-M.

4 Claims, 1 Drawing Sheet
Specification includes a Sequence Listing.

PHYTASE MUTANTS

CROSS-REFERENCE TO RELATED APPLICATIONS

This application is a divisional of U.S. application Ser. No. 15/524,390, filed on May 4, 2017, which is a national stage entry under 35 U.S.C. 371 of international application no. PCT/CN2014/093278 filed on Dec. 8, 2014, which claims priority to Chinese application No. 201410677220.8, named "Phytase mutants", filed on Nov. 21, 2014, the contents of all of the above are fully incorporated herein by reference.

REFERENCE SEQUENCE LISTING SUBMITTED AS A TEXT FILE

This application includes a Sequence Listing as a text file named "101788-1261327-000110US_SL.txt" created on Jul. 21, 2021 and containing 27,204 bytes. The material contained in this text file is incorporated by reference.

FIELD OF THE INVENTION

The present invention relates to biotechnology field, and particularly relates to phytase mutants, the method for producing the mutants and the uses thereof. The present invention also relates to DNA molecules encoding the mutants, expression vectors, and host cells.

BACKGROUND OF THE INVENTION

Phytase is a type of phosphatase enzyme and can hydrolyze phytate phosphorus (myo-inositol hexakisphosphate) into myo-inositol and inorganic phosphate. There are two types of phytase: 3-phytase (EC 3.1.3.8) and 6-phytase (EC 3.1.2.6). Phytase is widely spread in nature, occurring in plants, animals and microorganisms, including higher plants such as maize and wheat, prokaryotic microbes such as *Bacillus subtilis, Pseudomonas, Lactobacillus* and *Escherichia coli*, eukaryotic microbes such as yeast, *Rhizopus* and *Aspergillus*.

Phytate phosphorus is a major component of all plant seeds, constituting 1%-3% by weight of many cereals, beans and oilseeds and typically accounting for 60%-80% of the total phosphorus. However, mono gastric animals metabolize only 0%-40% of the phytate phosphorus since they lack digestive enzymes for phytate, which results in a number of problems. First of all, phosphorus source are wasted. On one hand, phytate phosphorus source in feed cannot be efficiently utilized; on the other hand, in order to ensure that the animals' requirement for phosphorus, it is necessary to add inorganic phosphorus in feed, which increases the feed costs. Secondly, the excreta with high phosphorus pollute the environment. 85% of the phytate phosphorus in feed will be directly excreted by animals, and the excreta containing high phytate phosphorus will pollute the water and soil seriously. In addition, phytate phosphorus is also a kind of antinutrient, which binds to several metallic ions such as $Zn^{2+}$, $Ca^{2+}$, $Cu^{2+}$ and $Fe^{2+}$ and other proteins to form insoluble compositions, preventing or inhibiting the absorption of the nutrients in the gastrointestinal tract, and reduces the effective utilization of nutrients.

Phytase can be used as a feed additive for mono gastric animals, and the feeding effect has been worldwide confirmed. Phytase can improve the phosphorus availability of plant feeds by 60% and decrease the phosphorus excretion by 40%. Phytase also can counteract the anti-nutritional properties of phytate. Therefore, the addition of phytase in animal feed is helpful for improving the production efficiency of livestock and poultry industry and for reducing the environmental pollution caused by phytate.

There are two main kinds of phytase for industrial production, one of which is fungal phytase derived from *Aspergillus niger* and the other is bacterial phytase derived from *E. coli*. The phytase APPA derived from *E. coli* has high specific activity and good gastrointestinal stability, and can be used in the feed industry by addition to mash feed directly or spraying on pelleted feed.

Bacterial phytase APPA has lower heat stability, the retention rate of which was even less than 30% after 70 degree Celsius (° C.) for 5 minutes in water bath. Thus there is a restriction of adding phytase directly into feed processing due to its low resistance on high temperature of 80-90° C. in feed pelleting period. However, there are still several disadvantages of applying liquid spraying technology using phytase, such as high equipment cost, less stability and uniformity of enzymes in the feed. Therefore it is of great importance to improve thermostability of phytase for feed.

SUMMARY OF THE INVENTION

This invention provides phytase mutants and the production methods thereof. The phytase mutants have enhanced thermostabilities, which is conducive to the wide applications of the phytase mutants in the feed field.

This invention provides phytase mutants comprising the amino acid sequences shown in (I) and (II):

(I) an amino acid sequence which has at least 70% identity to the amino acid sequence of the wild-type phytase;

(II) an amino acid sequence which has at least one immune epitope of the phytase, and comprises a modification, substitution, deletion, and/or insertion of one or more amino acids within the amino acid sequence of the wild-type phytase.

In some embodiments of the invention, the phytase mutants comprise amino acid sequences which have at least 75% identity to the amino acid sequence of the wild-type phytase.

In other embodiments, the phytase mutants comprise amino acid sequences which have at least 80% identity to the amino acid sequence of the wild-type phytase.

In other embodiments, the phytase mutants comprise amino acid sequences which have at least 85% identity to the amino acid sequence of the wild-type phytase.

In other embodiments, the phytase mutants comprise amino acid sequences which have at least 90% identity to the amino acid sequence of the wild-type phytase.

In other embodiments, the phytase mutants comprise amino acid sequences which have at least 95% identity to the amino acid sequence of the wild-type phytase.

In some embodiments, the modifications include amidation, phosphorylation, methylation, acetylation, ubiquitination, glycosylation, or carbonylation.

In other embodiments, the phytase mutants comprise 1, 2, 3, 4, 5, 6, 7, 8, 9, 10, 11, 12, 13, 14, 15, 16 or 17 amino acid substitutions within the amino acid sequence encoding the phytase.

In some embodiments of the invention, the phytase mutants comprise 12, 13, 16 or 17 amino acid substitutions within the amino acid sequence of the wild-type phytase.

In other embodiments, the phytase mutants have one or more amino acid substitutions in a position selected from position 25, 46, 62, 70, 73, 75, 114, 137, 142, 146, 159 and 255, the positions corresponding to the respective position in the amino acid sequence of the wild-type phytase.

In some embodiments of the invention, the amino acid sequence of the wild-type phytase is SEQ ID NO: 1.

In further embodiments, the phytase mutants comprise 12 amino acid substitutions, wherein the amino acid substitutions are in positions 25, 46, 62, 70, 73, 75, 114, 137, 142, 146, 159 and 255, and the substitutions are 25F, 46E, 62W, 70E, 73P, 75C, 114H, 137V, 142R, 146E, 159Y and 255D, the position corresponding to the respective position in SEQ ID NO: 1.

The invention also provides DNA molecules comprising a polynucleotide sequence encoding a phytase mutant described herein.

In other embodiments, the phytase mutants have amino acid sequences of SEQ ID NO: 3 or SEQ ID NO: 5 or SEQ ID NO: 7 or SEQ ID NO: 9.

In other embodiments, the DNA molecules encoding phytase mutants have polynucleotide sequences of SEQ ID NO: 4 or SEQ ID NO: 6 or SEQ ID NO: 8 or SEQ ID NO: 10.

The invention also provides vectors containing the DNA molecules encoding phytase mutants.

In other embodiment, the phytase mutant has the amino acid sequence of SEQ ID NO: 3, and one of the polynucleotide sequences encoding the same is SEQ ID NO: 4.

The invention also provides the plasmid containing the polynucleotide sequence of SEQ ID NO: 4.

In other embodiments, the phytase mutants also comprise amino acid substitutions in position 380, the position corresponding to the respective position in SEQ ID NO: 1.

In other embodiments, the amino acid substitution in position 380 is 380P (from Ala to Pro).

In other embodiment, the phytase mutant has the amino acid sequence of SEQ ID NO: 5, and one of the polynucleotide sequences encoding the same is SEQ ID NO: 6.

The invention also provides plasmids containing the polynucleotide sequence of SEQ ID NO: 6.

In other embodiments, the phytase mutants also comprise one or more amino acid substitutions in position 80, 176 and 187, the position corresponding to the respective position in SEQ ID NO: 1.

In other embodiments, the amino acid substitution in position 80 is 80P (from Ser to Pro), the amino acid substitution in position 176 is 176P (from Asn to Pro), the amino acid substitution in position 187 is 187P (from Ser to Pro).

In other embodiment, the phytase mutant has the amino acid sequence of SEQ ID NO: 7, and one of the polynucleotide sequences encoding the same is SEQ ID NO: 8.

The invention also provides plasmids containing the polynucleotide sequence of SEQ ID NO:8.

In other embodiments, the phytase mutants also comprise the amino acid substitutions in position 161, the position corresponding to the respective position in SEQ ID NO: 1.

In other embodiments, the amino acid substitution in position 161 is 161P (from Thr to Pro).

In other embodiment, the phytase mutant has the amino acid sequence of SEQ ID NO: 9, and one of the polynucleotide sequences encoding the same is SEQ ID NO: 10.

The invention also provides plasmids containing the nucleic acid sequence of SEQ ID NO:10.

The invention also provides the methods of producing the phytase mutants, which include:

Step 1: obtain a DNA molecule comprising a polynucleotide sequence encoding any one of the amino acid sequences shown in (I) and (II):

(I) an amino acid sequence which has at least 70% identity to the amino acid sequence of a wild-type phytase;

(II) an amino acid sequence which has at least one immune epitope of the phytase, and comprise a modification, substitution, deletion, and/or insertion of one or more amino acids of the amino acid sequence of the phytase.

Step 2: fuse the DNA molecule obtained by step 1 to the expression vectors, construct recombinant expression vectors, and transform the recombinant expression vectors into the host cells;

Step 3: induce the host cells containing recombinant expression vectors to express the fusion protein, and then isolate and purify the fusion protein.

In some embodiments of the invention, the modifications in the method of producing the phytase mutants include amidation, phosphorylation, methylation, acetylation, ubiquitination, glycosylation, or carbonylation.

In other embodiments, the substitutions in the method of producing the phytase mutants include 1, 2, 3, 4, 5, 6, 7, 8, 9, 10, 11, 12, 13, 14, 15, 16 or 17 amino acid substitutions within the amino acid sequence of the phytase.

In other embodiments, the substitutions in the method of producing the phytase mutants include one or more amino acid substitutions in a position selected from position 25, 46, 62, 70, 73, 75, 114, 137, 142, 146, 159 and 255, the positions corresponding to the respective position in the amino acid sequence of the phytase.

In other embodiments, the substitutions in the method of producing the phytase mutants also include amino acid substitutions in position 380, the positions corresponding to the respective position in the amino acid sequence encoding the phytase.

In other embodiments, the substitutions in the method of producing the phytase mutants further include one or more amino acid substitutions in position 80, 176 and 187, the positions corresponding to the respective position in the amino acid sequence of the phytase.

In other embodiments, the substitutions in the method of producing the phytase mutants further include amino acid substitutions in position 161, the positions corresponding to the respective position in the amino acid sequence of the phytase.

In some embodiments, the DNA molecules in step 1 of the method are obtained by amplification reactions of cDNA encoding the amino acid sequence of SEQ ID NO:3 or SEQ ID NO:5 or SEQ ID NO:7 or SEQ ID NO:9.

The host cell in Step 2 of the method is *Pichia*.

The invention also provides a modified feed such as feed for mono gastric animals comprising an effective amount of a phytase mutant described herein.

The invention also provides host cells containing the recombinant expression vectors.

In some embodiments, the host cell is *Pichia*.

The recombinant phytase mutants expressed in the *Pichia* containing the plasmid are more heat-resistant.

The invention provides phytase mutants comprising any one of the amino acid sequences shown in (I) and (II):

(I) an amino acid sequence which has at least 70% identity to the amino acid sequence of a wild-type phytase;

(II) an amino acid sequence which has at least one immune epitope of the phytase, and comprise a modification, substitution, deletion, and/or insertion of one or more amino acids of the amino acid sequence of the phytase.

There are four phytase mutants provided in the invention with improved heat resistance. After being treated at 75° C. for 5 minutes, the residual enzyme activity of the mutant APPA-M was higher than 95%, while that of the wild-type phytase APPA was lower than 10%. Using the mutant APPA-M as a basis, the invention also provided an additional one-point mutant PHY1 (A380P), an additional four-point mutant PHY4 (S80P, T161P, N176P and A380P) and an additional five-point mutant PHY5 (S80P, T161P, N176P, S187P and A380P). After being treated at 80° C. for 10 min, the residual enzyme activities of the mutants PHY1, PHY4 and PHY5 were higher by 33.85%, 53.11% and 75.86% respectively compared with that of APPA-M. After being treated at 85° C. for 5 min, the residual enzyme activities of the mutants PHY1, PHY4 and PHY5 were higher by 14.89%, 28.45% and 44.94% respectively compared with that of APPA-M. The heat resistance of these mutants are significantly higher than that of APPA-M, which will improve the applications of the phytase mutants in feed.

BRIEF DESCRIPTIONS OF DRAWINGS

EMBODIMENT

Figure 1:
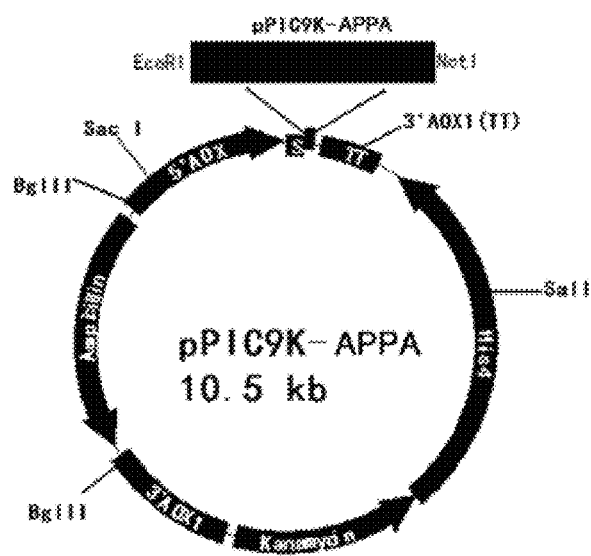
FIG. 1 shows the map of recombinant plasmid pPIC9K-APPA.

The invention discloses phytase mutants, methods of production and the uses thereof, DNA molecules encoding the mutants, vectors, and host cells. Technicians having ordinary skill in the field can learn from the contents of this invention and improve the process parameters to realize it. It is particularly to be noted that all similar substitutions and modifications will be regarded as obvious and are considered to be included in the invention. The invention has described the methods and applications in the preferred embodiments, and technicians in this field can readily modify or appropriately modify and combine the methods and Zo applications to realize and apply the invention without departing from the contents, spirit and scope of the invention.

Conventional techniques and methods in the field of genetic engineering and molecular biology are used in the invention, for example, the methods recorded in MOLECULAR CLONING: A LABORATORY MANUAL, 3nd Ed. (Sambrook, 2001) and CURRENT PROTOCOLS IN MOLECULAR BIOLOGY (Ausubel,2003). These general references provide one of skill with a general dictionary of many of the terms used in this invention. Based on the technical scheme described in the invention, all technical and scientific terms can choose other conventional methods, experimental programs and reagents to realize the invention, not limited to that described in the embodiments of the invention. For example, the following experimental materials and reagents can be used in the invention:

Strains and vectors: E. coli DH5a, Pichia pastoris strain GS115, vector pPIC9k were purchased from Invitrogen.

Reagents: Amp and G418 were purchased from Invitrogen.

Enzymes and Kits: PCR enzymes and ligases were purchased from Takara;

restriction endonucleases were purchased from Fermentas; plasmid mini kit and gel extraction kit were purchased from Omega; geneMorph II random mutagenesis kit was purchased from MBL Beijing Biotech Co., Ltd.

Medium recipes:

Lariant broth (LB medium): 0.5% yeast extract, 1% tryptone, 1% NaCl, pH7.0;

LB-AMP medium: LB medium with 100 μg/mL ampicillin;

Yeast extract peptone dextrose medium (YPD medium): 1% yeast extract, 1% tryptone, 1% glucose;

Minimal dextrose medium (MD medium): 2% tryptone, 2% agar;

BMGY medium: 2% tryptone, 1% yeast extract, 100 mM potassium phosphate buffer (pH 6.0), 1.34% YNB, $4\times10^{-5}$ biotin, 1% glycerol;

BMMY medium: 2% tryptone, 1% yeast extract, 100 mM potassium phosphate buffer (pH 6.0), 1.34% YNB, $4\times10^{-5}$ biotin, 1% methanol.

The invention was further illustrated by the following examples:

Example 1 Phytase Mutants

Gene Synthesis of the Wild-Type Phytase APPA and Phytase Mutant APPA-M

The wild-type phytase APPA was derived from E. coli, of which the amino acid sequence was SEQ ID NO:1 and the encoding polynucleotide sequence was SEQ ID NO: 2. In order to improve the thermostability of APPA, a phytase mutant was obtained by introducing 12 point-mutations into the amino acid sequence of SEQ ID NO:1, which were A25F, W46E, Q62W, G70E, A73P, K750, T114H, N137V, D142R, S146E, R159Y, Y255D.

The phytase mutant was named APPA-M, of which the amino acid sequence was SEQ ID NO: 3 and the encoding polynucleotide sequence was SEQ ID NO: 4. The polynucleotide sequence was optimized according to the codon preference of Pichia pastoris and synthesized by Shanghai Generay Biotech Co., Ltd with an EcoRI restriction site and a NotI restriction site added to the 5' end and 3' end respectively.

The same method above was used to synthesize the polynucleotide sequence of the wild-type phytase APPA.

Construction of the Expression Vector Carrying Phytase Gene

The two polynucleotide sequences synthesized in example 1.1 and the plasmid pPIC-9k were first digested by EcoRI and NotI, and then ligated together at 16° C. overnight respectively. After that, the recombinant plasmid was transformed into E. coli DH5a. The recombinant E. coli strains then were spread onto LB+Amp plates. The plates were placed inverted and incubated at 37° C. until transformants grew up. Positive transfromants were selected and verified by colony PCR and DNA sequencing, and named as pPIC9K-APPA (the map of pPIC9K-APPA were shown in FIG. 1) and pPIC9K-APPA-M respectively. The reaction system of colony PCR contained: monoclonal sample, rTaqDNA polymerase 0.5 ul, 10×Buffer 2.0 μL, dNTPs (2.5 mM) 2.0 μL, 5'AOX primer (10M) 0.5 μL, 3'AOX primer 0.5 μL, ddH2O 14.5 μL; PCR conditions were: 95° C. for 5 min (1 cycle), 94° C. for 30 sec, 55° C. for 30 sec, 72° C. for 2 min (30 cycles), and 72° C. for 10 min (1 cycle).

Construction of the Recombinant P. pastoris Strains

Preparation of Competent P. pastoris Cells

Host cells P. pastoris GS115 were spread onto YPD plates and the plates were incubated at 30° C. for 48 h. GS115 colonies were picked up and inoculated into 6 mL YPD liquid medium and incubated for approximately 12 h at 30° C. with shaking at 220 rpm. Then the YPD liquid medium containing GS115 was inoculated into 30 mL YPD liquid medium and incubated for 5 h at 30° C. with shaking at 220 rpm. The cell density of the yeast cultures were measured using a spectrophotometer. When the optical density (OD600) between 1.1 and 1.3, 4 mL yeast cultures were added into a sterilized EP tubes and centrifuged at 9000 rpm and 4° C. for 2 min. The supernatants were removed, while the remaining yeast cells were re-suspended in 1 ml of sterile pre-cooled water. The suspension containing yeast cells was centrifuged at 9000 rpm and 4° C. for 2 min. The supernatant was removed, while the remaining yeast cells were re-suspended in 1 ml of pre-cooled sorbitol (1 mol/L). The sorbitol containing yeast cells was centrifuged at 9000 rpm and 4° C. for 2 min. The supernatant was removed, while the remaining yeast cells were re-suspended in 100-150 μl of sterile pre-cooled sorbitol (1 mol/L).

1.3.2 Transformation and Screening

The recombinant plasmids pPIC9K-APPA and pPIC9K-APPA-M were linearized by Sal I and transformed into *Pichia pastoris* GS115 respectively by electroporation. Then the transformation mixtures were spread on MD plates and dried in a sterile bench. The MD plates were placed inverted and incubated at 30° C. for 2-3 days to obtain recombinant *P. pastoris* strains carrying the recombinant plasmids pPIC9K-APPA or pPIC9K-APPA-M. There were approximately 300 clones on each plate. The clones were washed down with sterile water and spread on YPD plates containing different concentrations of geneticin (0.5 mg/mL-8 mg/mL) to screen multiple copies of transformants.

One of the recombinant yeast strains carrying the recombinant plasmids pPIC9K-APPA was named *Pichia pastoris* APPA. One of the recombinant yeast strains carrying the recombinant plasmids pPIC9K-APPA-M was named *Pichia pastoris* APPA-M. The two recombinant strains were first inoculated into separate flasks with BMGY medium and cultured at 30° C. for 1 d with agitation at 250 rpm, and then inoculated in BMMY medium at 30° C. for 4d with agitation at 250 rpm. 0.5% methanol was added into the medium as an inducer every day. After that, the medium was centrifuged at 9000 rpm for 10 min. The fermentation supernatants containing phytase were retained, while the yeast cells were removed.

(1) Definition of Phytase Activity Unit

One phytase unit is the activity of phytase that generates 1 micromole of inorganic phosphorus per minute from 5.0 mmol/L sodium phytate at pH 5.0 and 37° C., which is indicated as U.

Method for Detecting Phytase Activity 1.8 mL of acetic acid buffer (pH 5.0) and 0.2 mL of sample are both added into two separate cuvettes named A and B, mixed and warmed at 37° C. for 5 min. 4 mL of substrate solution is added into cuvette A and 4 mL of stop solution is added into cuvette B, mixed and reacted at 37° C. for 30 min. The reaction is ended by adding and mixing 4 mL stop solution in cuvette A and 4 mL substrate solution in cuvette B. After standing for 3 min, the absorbance is measured at 415 nm. Three repeats are made for each sample, and the average of the absorbance values is used for calculating the phytase activity by regression linear.

Enzyme activity: $X = F \times C/(m \times 30)$ where: X—Unit of enzyme activity, U/g (mL);
F—Total dilution factors of sample solution before reaction;
C—The enzyme activity is calculated from the linear regression equation based on the absorbance of the actual sample solution, U;
m—Sample mass or volume, g/mL;
30—Reaction time;

(3) Phytase activities were shown in Table 1

TABLE 1

| | Phytase activities | | | | |
|---|---|---|---|---|---|
| Sample | Value 1 | Value 2 | Value 3 | Average | Activity (U/mL) |
| APPA | 0.473 | 0.477 | 0.471 | 0.474 | 166 |
| APPA-M | 0.486 | 0.489 | 0.484 | 0.486 | 195 |

As shown in Table 1, the enzyme activities of the fermentation supernatants of *Pichia pastoris* APPA and *Pichia pastoris* APPA-M were 166 U/mL and 195 U/mL, respectively.

Fermentation Process

*P. pastoris* APPA and *P. pastoris* APPA-M were cultured in two separate 10 L fermenters with the fermentation medium containing: 1.1 g/L $CaSO_4$, 5.5 g/L $KH_2PO_4$, 55 g/L $NH_4H_2PO_4$, 16.4 g/L $MgSO_4$, 20.3 g/L $K_2SO_4$, 1.65 g/L KOH and 0.05% antifoam, and the fermentation parameters: pH 5.0, 30° C., agitation at 300 rpm, aeration at 1.0-1.5 v/v, and the dissolved oxygen kept above 20%.

There were three stages of the fermentation process. The first stage was for cell culture with 7% seed inoculated and cultured at 30° C. for 24-26 h until the supplement of glucose was finished. The second stage was for cell hunger with no more carbon source supplemented. This stage lasted about 30-60 min until the concentration of dissolved oxygen rose to 80%. The third stage was for inducing the expression of phytase with methanol added as an inducer in flow, and the concentration of dissolved oxygen maintained at more than 20%, which lasted about 150-180 h. After that, the fermentation broth was treated by a plate and frame filter to obtain crude enzyme solution.

The phytase activities of the crude enzyme solutions were determined by the method mentioned in 1.3.2, and the results were shown in Table 2.

TABLE 2

| | Phytase activity test results | | | | |
|---|---|---|---|---|---|
| Sample | Value 1 | Value 2 | Value 3 | Average | Activity (U/mL) |
| APPA | 0.488 | 0.485 | 0.487 | 0.487 | 9800 |
| APPA-M | 0.459 | 0.461 | 0.462 | 0.461 | 10257 |

The phytase activities of the crude enzyme solutions of *P. pastoris* APPA and *P pastoris* APPA-M were 9800 U/mL and 10257 U/mL, respectively.

Analysis of Enzymatic Properties

Optimal Temperature

The phytase activities of the crude enzyme solutions of *P. pastoris* APPA and *P pastoris* APPA-M were measured at pH5.5 and 5° C. intervals between 30° C. and 85° C. With the highest phytase activity calculated 100%, the relative enzyme activities were calculated. The results showed that the optimal temperatures of the wild-type phytase APPA and phytase mutant APPA-M were both 75° C.

Optimal pH

The crude enzyme solutions of *P. pastoris* APPA and *P. pastoris* APPA-M were diluted by 0.1M acetic acid-sodium acetate buffer at pH 2.0, 2.5, 3.0, 3.5, 4.0, 4.5, 5.0, 5.5, 6.0, 6.5, 7.0 respectively. The phytase activities were measured at 37° C., and the relative enzyme activities were calculated with the highest enzyme activity calculated 100%. The results showed that the optimal pH of wild phytase APPA and phytase mutant APPA-M was both 5.0.

Thermostability

The crude enzyme solutions of *P. pastoris* APPA and *P. pastoris* APPA-M were diluted 10 times with 0.25M sodium acetate buffer (pH 5.0) which was preheated for 10 min. The diluted enzyme solutions were well mixed and treated at 75° C. for 5 min. The phytase activities were measured when the diluted enzyme solutions were cooled to room temperature. With the phytase activity of the untreated enzyme solution calculated 100%, the residual phytase activities were calculated.

Residual phytase activity (%)=phytase activity of the enzyme solution being treated/phytase activity of the enzyme solution being untreated×100%.

The results showed that after being treated at 75° C. for 5 min, the residual phytase activity of the wild-type phytase APPA was below 10%, while that of the phytase mutant APPA-M was above 95%. In conclusion, the thermostability of the phytase mutant APPA-M was significantly higher than that of the wild-type phytase APPA.

Example 2 Phytase Mutants

In order to improve the thermostability of the phytase mutant APPA-M, the protein structure of APPA-M was analyzed. The result showed that there were two domains in the protein: domain I contained 134 amino acid residues at the N-terminus and 152 amino acid residues at C-terminus, while domain II contained the remaining 124 amino acid residues in the middle. The conserved sequences and activity center are all in domain I. Without destroying the secondary structure and activity center of the protein, Further mutations of the amino acid residuals were carried out.

2.1 Mutations of Phytase Mutant APPA-M

```
Primer APPAM-FI and APPAM-R1 were designed:
XynII-F1: GGCGAATTC CAGTCAGAACCAGAGTTGAAGTT
(Underlined was the recognition site of
restriction endonuclease EcoRI),
which was shown in SEQ ID NO: 11;

XynII-R1: ATAGCGGCCGCTTACAAGGAACAAGCAGGGAT
(Underlined was the recognition site of
restriction endonuclease NotI),
which was shown in SEQ ID NO: 12;
```

APPA-M gene was amplified using the primers above by a GeneMorph II random mutagenesis kit. The amplification products were recovered, and then digested with EcoRI and NotI and ligated into EcoRI-NotI-digested plasmid pET21a. After that the plasmid was transformed into *E. coli* BL21 (DE3) and then the recombinant *E. coli* cells were spread onto LB+Amp plates. After being incubated at 37° C., the colonies were transferred one by one into 96-well polypropylene microtiter plates containing LB+Amp medium with 150 ul 0.1 mM IPTG in each well. The microtiter plates were incubated at 37° C. for 6 h with shaking at 220 rpm. The supernatant was removed from the fermentation broth by centrifugation. Afterwards the cells were re-suspended with buffer and repeated freeze-thawed to obtain phytase-containing *E. coli* cell lysates.

40 ul cell lysates were transferred into two separate new 96-well plates, one of which was treated at 80° C. for 10 min, and the other was not. 80 ul substrates were added into each well of the plates and incubated for 30 min at 37° C. Afterwards 80 ul stop solution (ammonium vanadate: ammonium molybdate: nitric acid=1:1:2) was added to end the reaction. In each well of the plates, the contents of inorganic phosphate were determined, which reflected the activities of different mutants obtained in the invention.

Compared with phytase APPA-M, the thermostabilities of some mutants were not improved, or even worse. For example, after being treated at 80° C. for 5 min, the residual enzyme activities of a three-point mutant (Q184E/Y289K/I405L) and the C-terminal (CNZSMQTD) removed mutant were reduced by 9% and 17% respectively, and two one-point mutants (Q285Y and C178N) were almost inactivated. Besides, there were some mutants with improved thermostabilities, but their enzymatic properties were significantly changed, which also limited their applications in feed.

This invention provided three mutants with significantly improved thermostabilities as well as high activities and original enzymatic properties.

One mutant was named PHY1 with one-point mutation A380P, its amino acid sequence was shown as SEQ ID NO: 5, and the encoding polynucleotide sequence was shown as SEQ ID NO: 6.

Another mutant was named PHY4 with four-point mutations S80P, N176P, S187P and A380P, its amino acid sequence was shown as SEQ ID NO: 7, and the encoding polynucleotide sequence was shown as SEQ ID NO: 8.

The other mutant was named PHY5 with five-point mutations S80P, T161P, N176P, S187P and A380P, its amino acid sequence was shown as SEQ ID NO: 9, and the encoding polynucleotide sequence was shown as SEQ ID NO: 10.

2.2 Synthesis and Amplification of Mutant Genes

Three polynucleotide sequences were synthesized with reference to SEQ ID NO: 6, SEQ ID NO: 8 and SEQ ID NO: 10 and optimized based on codon bias of *Pichia Postoris* by Shanghai Generay Biotech Co., Ltd, of which an EcoRI restriction site and a NotI restriction site were added to the 5' end and 3' end respectively.

2.3 Construction of Expression Vector

The three polynucleotide sequences synthesized above and the plasmids pPIC-9k were first digested by EcoRI and NotI, and then ligated together at 16° C. overnight respectively. After that, the recombinant plasmid was transformed into *E. coli* DH5a. The recombinant *E. coli* cells then were spread onto LB+Amp plates. The plates were placed inverted and incubated at 37° C. until transformants grew up. Positive transfromants were selected and verified by colony PCR (reaction was as same as in Example 1) and DNA sequencing, and were named as pPIC9K-PHY1, pPIC9K-PHY4 and pPIC9K-PHY5 respectively.

2.4 Construction of the Recombinant *P. pastoris* Strain

The recombinant plasmids pPIC9K-PHY1, pPIC9K-PHY4 and pPIC9K-PHY5 were linearized by Sal I and transformed into host cells *Pichia pastoris* GS115 by electroporation. The recombinant strains *P. pastoris* GS115/pPIC9K-PHY1, GS115/pPIC9K-PHY4 and GS115/pPIC9K-PHY5 were obtained on MD plates after screening YPD plates containing different concentrations of geneticin (0.5 mg/mL-8 mg/mL) were used to select multiple copies of transformants.

The transformants of the recombinant strains GS115/pPIC9K-PHY1, GS115/pPIC9K-PHY4 and GS115/pPIC9K-PHY5 were named *Pichia pastoris* PHY1, *Pichia pastoris* PHY4, and *Pichia pastoris* PHY5, respectively. The three transformants above were inoculated into separate flasks with BMGY medium and cultured at 30° C. for 1 d with agitation at 250 rpm, and then transferred and inoculated in BMMY medium at 30° C. for 4d with agitation at 250 rpm. 0.5% methanol, as an inducer, was added every 24 h. The cells were removed from the fermentation broth by centrifugation at 9000 rpm for 10 min and the fermentation supernatants containing phytase PHY1, or phytase PHY4 or phytase PHY5 were retained.

The activities of fermentation supernatants were detected by the method mentioned in 1.3.2, and the results were shown in Table 3.

TABLE 3

| Phytase activities | | | | | |
|---|---|---|---|---|---|
| Sample | Value 1 | Value 2 | Value 3 | Average | Activity (U/mL) |
| PHY1 | 0.481 | 0.483 | 0.484 | 0.482 | 211 |
| PHY4 | 0.483 | 0.479 | 0.481 | 0.481 | 201 |
| PHY5 | 0.491 | 0.488 | 0.489 | 0.489 | 255 |

As shown in Table 3, the activities of the fermentation supernatants of *Pichia pastoris* PHY1, PHY4 and PHY5 were 211 U/mL, 201 U/mL and 255 U/mL, respectively.

2.5 Fermentation Process

*P. pastoris* PHY1, *P. pastoris* PHY4 and *P. pastoris* PHY5 were fermented in three separate 10 L fermenters. The fermentation medium contained 1.1 g/L $CaSO_4$, 5.5 g/L $KH_2PO_4$, 55 g/L $NH_4H_2PO_4$, 16.4 g/L $MgSO_4$, 20.3 g/L $K_2SO_4$, 1.65 g/L KOH and 0.05% antifoam.

Fermentation parameters: pH 5.0, 30° C., agitation at 300 rpm, aeration at 1.0-1.5 v/v, and the dissolved oxygen was kept above 20%.

There were three stages of the fermentation process. The first stage was for cell culture with 7% seed inoculated and cultured at 30° C. for 24-26 h until the supplement of glucose was finished. The second stage was for cell hunger with no more carbon source supplemented. This stage lasted about 30-60 min until the concentration of dissolved oxygen rose to 80%. The third stage was for inducing the expression of phytase with methanol added as an inducer in flow, and the concentration of dissolved oxygen maintained at more than 20%, which lasted about 150-180 h. After that, the fermentation broth was treated by a plate and frame filter to obtain crude enzyme solution.

The phytase activities of the crude enzyme solutions were detected by the method mentioned in 1.3.2, and the results were shown in Table 4.

TABLE 4

| Phytase activities | | | | | |
|---|---|---|---|---|---|
| Sample | Value 1 | Value 2 | Value 3 | Average | Activity (U/mL) |
| PHY1 | 0.478 | 0.479 | 0.481 | 0.479 | 10317 |
| PHY4 | 0.484 | 0.480 | 0.481 | 0.482 | 10401 |
| PHY5 | 0.479 | 0.477 | 0.480 | 0.479 | 10813 |

The phytase activities of the crude enzyme solutions of *P. pastoris* PHY1, *P. pastoris* PHY4 and *P. pastoris* PHY5 were 10317 U/mL, 10401 U/mL, and 10813 U/mL, respectively.

Analysis of Enzymatic Properties

Optimal Temperature

The phytase activities of the crude enzyme solutions of *P. pastoris* PHY1, PHY4 and PHY5 were measured at pH5.5 and 5° C. intervals between 30° C. and 85° C. With the highest phytase activity calculated 100%, the relative enzyme activities were calculated. The results showed that the optimal temperatures of phytase mutants PHY1, PHY4 and PHY5 were 75° C., which were the same with the wild-type phytase APPA and the mutant APPA-M.

Optimal pH

The crude enzyme solutions of *P. pastoris* PHY1, PHY4 and PHY5 were diluted by 0.1M acetic acid-sodium acetate buffer at pH 2.0, 2.5, 3.0, 3.5, 4.0, 4.5, 5.0, 5.5, 6.0, 6.5, 7.0 respectively. The phytase activities were measured at 37° C., and the relative enzyme activities were calculated with the highest enzyme activity calculated 100%. The results showed that the optimal pH of the phytase mutants PHY1, PHY4 and PHY5 were 5.0, which were the same with the wild-type phytase APPA and the mutant APPA-M.

Thermostability

The crude enzyme solutions of *P. pastoris* PHY1, PHY4 and PHY5 were diluted 10 times with 0.25M sodium acetate buffer (pH 5.0) which was preheated for 10 min. The diluted enzyme solutions were well mixed and treated at 85° C. for 5 min, and 80° C. for 10 min, respectively. The phytase activities were measured when the diluted enzyme solutions were cooled to room temperature. With the phytase activity of the untreated enzyme solution calculated 100%, the residual phytase activities were calculated.

Figure 2:
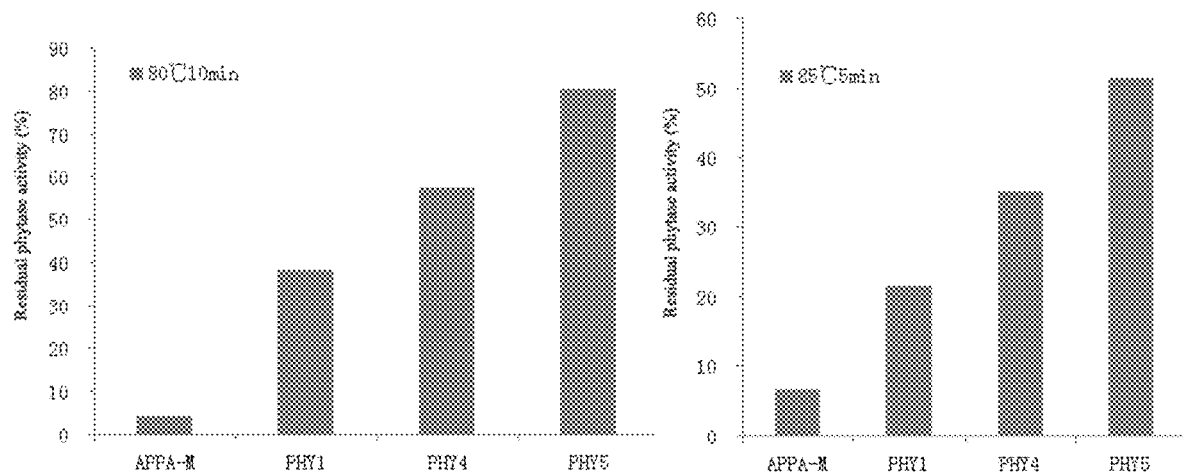
FIG. 2 shows the thermostability of PHY1, PHY4 and PHY5 compared with that of APPA-M.

As shown in FIG. 2, compared with phytase mutant APPA-M, the residual activity of the phytase mutants PHY1, PHY4 and PHY5 were higher by 33.85%, 53.11% and 75.86%, respectively, after being treated at 80° C. for 10 min, and were higher by 14.89%, 28.45% and 44.94%, respectively, after treating at 85° C. for 5 min.

In conclusion, Using the mutant APPA-M as a basis, the invention provided new mutants containing additional one- or multiple-point mutations such as a one-point mutant PHY1 (A380P), a four-point mutant PHY4 (S80P, T161P, N176P and A380P) and a five-point mutant PHY5 (S80P, T161P, N176P, S187P and A380P). Compared with phytase mutant APPA-M, the optimal pH of the phytase mutants PHY1, PHY4 and PHY5 remained unchanged, but the thermostabilities of the phytase mutants PHY1, PHY4 and PHY5 had been significantly increased, which was conducive to the applications of the phytase mutants in feed.

The phytase mutants provided herein are described in detail. The principles and embodiments of the invention have been described with reference to specific examples, and the descriptions of the above embodiments are merely illustrative of the method and the core idea of the present invention. It is particularly to be noted that all similar substitutions and modifications without departing from the principle will be regarded as obvious to those skilled in the field and are considered to be fallen within the scope of the claims of the invention.

```
SEQUENCE LISTING

<110> Qingdao Vland Biotech Group Co., Ltd.

<120> Phytase mutants

<130> 0P140901

<160> 12

<170> PatentIn version 3.3
```

```
<210> 1
<211> 410
<212> PRT
<213> phytase
<400> 1
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400
```

Asn Glu Ala Arg Ile Pro Ala Cys Ser Leu
            405                 410

<210> 2
<211> 1233
<212> DNA
<213> phytase
<400> 2

| | | | | | |
|---|---|---|---|---|---|
| cagagtgagc | cggagctgaa | gctggaaagt | gtggtgattg | tcagtcgtca | tggtgtgcgt | 60 |
| gctccaacca | aggccacgca | actgatgcag | gatgtcaccc | cagacgcatg | gccaacctgg | 120 |
| ccggtaaaac | tgggttggct | gacaccgcgc | ggtggtgagc | taatcgccta | tctcggacat | 180 |
| taccaacgcc | agcgtctggt | agccgacgga | ttgctggcga | aaaagggctg | cccgcagtct | 240 |
| ggtcaggtcg | cgattattgc | tgatgtcgac | gagcgtaccc | gtaaaacagg | cgaagccttc | 300 |
| gccgccgggc | tggcacctga | ctgtgcaata | accgtacata | cccaggcaga | tacgtccagt | 360 |
| cccgatccgt | tatttaatcc | tctaaaaact | ggcgtttgcc | aactggataa | cgcgaacgtg | 420 |
| actgacgcga | tcctcagcag | ggcaggaggg | tcaattgctg | actttaccgg | gcatcggcaa | 480 |
| acggcgtttc | gcgaactgga | acgggtgctt | aattttccgc | aatcaaactt | gtgccttaaa | 540 |
| cgtgagaaac | aggacgaaag | ctgttcatta | acgcaggcat | taccatcgga | actcaaggtg | 600 |
| agcgccgaca | atgtctcatt | aaccggtgcg | gtaagcctcg | catcaatgct | gacggagata | 660 |
| tttctcctgc | aacaagcaca | gggaatgccg | gagccggggt | ggggaaggat | caccgattca | 720 |
| caccagtgga | acaccttgct | aagtttgcat | aacgcgcaat | tttatttgct | acaacgcacg | 780 |
| ccagaggttg | cccgcagccg | cgccaccccg | ttattagatt | tgatcaagac | agcgttgacg | 840 |
| ccccatccac | cgcaaaaaca | ggcgtatggt | gtgacattac | ccacttcagt | gctgtttatc | 900 |
| gccggacacg | atactaatct | ggcaaatctc | ggcggcgcac | tggagctcaa | ctggacgctt | 960 |
| cccggtcagc | cggataacac | gccgccaggt | ggtgaactgg | tgtttgaacg | ctggcgtcgg | 1020 |
| ctaagcgata | acagccagtg | gattcaggtt | tcgctggtct | tccagacttt | acagcagatg | 1080 |
| cgtgataaaa | cgccgctgtc | attaaatacg | ccgcccggag | aggtgaaact | gacccctgca | 1140 |
| ggatgtgaag | agcgaaatgc | gcagggcatg | tgttcgttgg | caggttttac | gcaaatcgtg | 1200 |
| aatgaagcac | gcataccggc | gtgcagtttg | taa | | | 1233 |

<210> 3
<211> 410
<212> PRT
<213> Artificial sequence
<400> 3
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
            115                 120                 125

Lys Thr Gly Val Cys Gln Leu Asp Val Ala Asn Val Thr Arg Ala Ile
    130                 135                 140

```
Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
            165                 170                 175

Leu Cys Leu Lys Arg Glu Lys Gln Asp Glu Ser Cys Ser Leu Thr Gln
        180                 185                 190

Ala Leu Pro Ser Glu Leu Lys Val Ser Ala Asp Asn Val Ser Leu Thr
    195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
            245                 250                 255

Leu Gln Arg Thr Pro Glu Val Ala Arg SerArg Ala Thr Pro Leu Leu
        260                 265                 270

Asp Leu Ile Lys Thr Ala Leu Thr Pro His Pro Pro Gln Lys Gln Ala
    275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
            325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> 4
<211> 1233
<212> DNA
<213> Artificial sequence
<400> 4
cagtcagaac cagagttgaa gttggagtca gtcgtcatcg ttagtagaca tggagttaga     60
gccctacaa agtttaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa agtgtggttg ccctcaatct    240
ggacaggttg caattatcgc tgatgttgat gaaagaacta gaaaaacagg agaggctttt    300
gctgccggat tggccccaga ttgtgcaatc actgttcatc accagccga tacatcttcc     360
ccagacccctt tgttcaaccc tcttaagaca ggagtctgtc agttggatgt tgccaatgtc    420
accagagcaa ttttggaaag agctggtgga agtatcgccg actttactgg tcactaccaa    480
acagctttca gagaattgga gagttctt aactttccac agtccaattt gtgtcttaag    540
agagaaaagc aagatgagtc atgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
```

```
                                   -continued
catcagtgga acactttgct ttctttgcac aatgctcaat tcgacttgct tcagagaact    780
ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac ctgataatac cccacctggt ggagaattgg tttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttgcc   1140
ggatgtgaag agagaaatgc acaaggaatg tgcagtcttg ctggtttcac ccaaatcgtc   1200
aatgaggcta gaatccctgc ttgttccttg taa                                1233
```

<210> 5
<211> 410
<212> PRT
<213> Artificial sequence
<400> 5

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg ThrArg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val ThrArg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg SerArg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300
```

```
Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> 6
<211> 1233
<212> DNA
<213> Artificial sequence
<400> 6
cagtcagaac cagagttgaa gttggagtca gtcgtcatcg ttagtagaca tggagttaga    60
gccctacaa agtttaccca gcttatgcaa gatgttaccc cagacgcttg gccaacttgg   120
cctgtcaagt tgggagaact tactcctaga ggtggagagt tgattgccta ccttggtcat   180
tattggagac aaagattggt tgcagatgaa ttgcttccaa agtgtggttg ccctcaatct   240
ggacaggttg caattatcgc tgatgttgat gaaagaacta gaaaaacagg agaggctttt   300
gctgccggat tggccccaga ttgtgcaatc actgttcatc accaagccga tacatcttcc   360
ccagaccctt tgttcaaccc tcttaagaca ggagtctgtc agttggatgt tgccaatgtc   420
accagagcaa ttttggaaag agctggtgga agtatcgccg actttactgg tcactaccaa   480
actgctttca gagaattgga gagagttctt aactttccac agtccaactt gtgtcttaag   540
agagaaaagc aagatgagtc ttgcagtttg actcaggctc ttccttctga gttgaaagtt   600
tccgccgaca acgtctcatt gaccggagct gtttctcttg cctccatgtt gactgaaatt   660
ttcttgcttc aacaggctca gggtatgcca gagcctggtt ggggaagaat accgatagt   720
catcagtgga acactttgct ttcttttgcac aatgctcaat tcgacttgct tcagagaact   780
ccagaagttg caagatccag agctacacct ttgcttgatc ttattaagac cgcattgact   840
ccacatccac ctcaaaaaca ggcttatgga gttacattgc ctacctctgt cttgttcatc   900
gctggtcacg acactaactt ggcaaatctt ggtggagctt tggagcttaa ctggacattg   960
ccaggtcaac tgataataca cccacctggt ggagaattgg ttttttgagag atggagaaga  1020
ttgtcagaca atagtcaatg gattcaggtt ccttggtct tccaaacttt gcaacagatg  1080
agagataaga ccattgtc acttaacacc ccacctggtg aagtcaaatt gacacttcct  1140
ggatgtgaag agaaaatgc acaaggaatg tgcagtcttg ctggtttcac ccaaatcgtc  1200
aatgaggcta gaatccctgc ttgttccttg taa                              1233

<210> 7
<211> 410
<212> PRT
<213> Artificial sequence
<400> 7
Gln Ser Glu Pro Glu Leu Lys Leu Glu Ser Val Val Ile Val SerArg
1                 5                  10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
        35                  40                  45
```

-continued

```
Pro Arg Gly Gly Glu Leu Ile Ala Tyr Leu Gly His Tyr Trp Arg Gln
        50                   55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
                115                 120                 125

Lys Thr Gly Val Cys Gln Leu Asp Val Ala Asn Val Thr Arg Ala Ile
        130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> 8
<211> 1233
<212> DNA
<213> Artificial sequence
<400> 8
cagtcagaac cagagttgaa gttggagtca gtcgtcatcg ttagtagaca tggagttaga    60 gccctacaa agtttaccca gcttatgcaa gatgttaccc cagacgcttg gccaacttgg   120
cctgtcaagt tgggagaact tactcctaga ggtggagagt tgattgccta ccttggtcat   180
```

```
tattggagac aaagattggt tgcagatgaa ttgcttccaa agtgtggttg ccctcaacca   240
ggacaggttg caattatcgc tgatgttgat gaaagaacta gaaaaacagg agaggctttt   300
gctgccggat tggccccaga ttgtgcaatc actgttcatc accaagccga tacatcttcc   360
ccagacccct tgttcaaccc tcttaagaca ggagtctgtc agttggatgt tgccaatgtc   420
accagagcaa ttttggaaag agctggtgga agtatcgccg actttactgg tcactaccaa   480
actgctttca gagaattgga gagagttctt aactttccac agtccccatt gtgtcttaag   540
agagaaaagc aagatgagcc atgcagtttg actcaggctc ttccttctga gttgaaagtt   600
tccgccgaca acgtctcatt gaccggagct gtttctcttg cctccatgtt gactgaaatt   660
ttcttgcttc aacaggctca gggtatgcca gagcctggtt ggggaagaat caccgatagt   720
catcagtgga acactttgct ttctttgcac aatgctcaat cgacttgct tcagagaact   780
ccagaagttg caagatccag agctacacct ttgcttgatc ttattaagac cgcattgact   840
ccacatccac ctcaaaaaca ggcttatgga gttacattgc ctacctctgt cttgttcatc   900
gctggtcacg acactaactt ggcaaatctt ggtggagctt tggagcttaa ctggacattg   960
ccaggtcaac tgataatac cccacctggt ggagaattgg tttttgagag atggagaaga  1020
ttgtcagaca atagtcaatg gattcaggtt tccttggtct tccaaacttt gcaacagatg  1080
agagataaga caccattgtc acttaacacc ccacctggtg aagtcaaatt gacacttcct  1140
ggatgtgaag agagaaatgc acaaggaatg tgcagtcttg ctggtttcac ccaaatcgtc  1200
aatgaggcta gaatccctgc ttgttccttg taa                                1233
```

<210> 9
<211> 410
<212> PRT
<213> Artificial sequence

<400> 9

Gln Ser Glu Pro Glu Leu Lys Leu Glu Ser Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg ThrArg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val ThrArg Ala Ile
    130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

```
Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg SerArg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> 10
<211> 1233
<212> DNA
<213> Artificial sequence
<400> 10
cagtcagaac cagagttgaa gttggagtca gtcgtcatcg ttagtagaca tggagttaga   60
gccccctacaa agtttaccca gcttatgcaa gatgttaccc cagacgcttg gccaacttgg  120
cctgtcaagt tgggagaact tactcctaga ggtggagagt tgattgccta ccttggtcat  180
tattggagac aaagattggt tgcagatgaa ttgcttccaa agtgtggttg ccctcaacca  240
ggacaggttg caattatcgc tgatgttgat gaaagaacta gaaaaacagg agaggctttt  300
gctgccggat tggccccaga ttgtgcaatc actgttcatc accaagccga tacatcttcc  360
ccagaccctt tgttcaaccc tcttaagaca ggagtctgtc agttggatgt tgccaatgtc  420
accagagcaa ttttggaaag agctggtgga agtatcgccg actttactgg tcactaccaa  480
ccagctttca gagaattgga gagttctt aactttccac agtccccatt gtgtcttaag  540
agagaaaagc aagatgagcc atgcagtttg actcaggctc ttccttctga gttgaaagtt  600
tccgccgaca acgtctcatt gaccggagct gtttctcttg cctccatgtt gactgaaatt  660
ttcttgcttc aacaggctca gggtatgcca gagcctggtg ggggaagaat caccgatagt  720
catcagtgga cactttgct ttctttgcac aatgctcaat tcgacttgct tcagagaact  780
ccagaagttg caagatccag agctcacacct ttgcttgatc ttattaagac cgcattgact  840
ccacatccac ctcaaaaaca ggcttatgga gttacattgc ctacctctgt cttgttcatc  900
gctggtcacg acactaactt ggcaaatctt ggtggagctt ggagcttaa ctggacattg  960
ccaggtcaac ctgataatac cccacctggt ggagaattgg ttttttgagag atggagaaga 1020
ttgtcagaca atagtcaatg gattcaggtt tccttggtct ccaaactttt gcaacagatg 1080
agagataaga caccattgtc acttaacacc ccacctggtg aagtcaaatt gacacttcct 1140
```

-continued

```
ggatgtgaag agagaaatgc acaaggaatg tgcagtcttg ctggtttcac ccaaatcgtc   1200
aatgaggcta gaatccctgc ttgttccttg taa                                1233

<210> 11
<211> 32
<212> DNA
<213> Artificial sequence
<400> 11
ggcgaattcc agtcagaacc agagttgaag tt                                   32

<210> 12
<211> 32
<212> DNA
<213> Artificial sequence
<400> 12
atagcggccg cttacaagga acaagcaggg at                                   32
```

SEQUENCE LISTING

<160> NUMBER OF SEQ ID NOS: 12

<210> SEQ ID NO 1
<211> LENGTH: 410
<212> TYPE: PRT
<213> ORGANISM: Escherichia coli

<400> SEQUENCE: 1

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255
```

```
Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
            405                 410

<210> SEQ ID NO 2
<211> LENGTH: 1233
<212> TYPE: DNA
<213> ORGANISM: Escherichia coli

<400> SEQUENCE: 2
cagagtgagc cggagctgaa gctggaaagt gtggtgattg tcagtcgtca tggtgtgcgt     60
gctccaacca aggccacgca actgatgcag gatgtcaccc cagacgcatg gccaacctgg    120
ccggtaaaac tgggttggct gacaccgcgc ggtggtgagc taatcgccta tctcggacat    180
taccaacgcc agcgtctggt agccgacgga ttgctggcga aaaagggctg cccgcagtct    240
ggtcaggtcg cgattattgc tgatgtcgac gagcgtaccc gtaaaacagg cgaagccttc    300
gccgccgggc tggtgcacct gctgtgcaat accgtacata cccaggcaga tacgtccagt    360
cccgatccgt tatttaatcc tctaaaaact ggcgtttgcc aactggataa cgcgaacgtg    420
actgacgcga tcctcagcag ggcaggaggg tcaattgctg actttaccgg cgcatcggca    480
acggcgtttc gcgaactgga cgggtgctt aattttccgc aatcaaactt gtgccttaaa    540
cgtgagaaac aggacgaaag ctgttcatta acgcaggcat taccatcgga actcaaggtg    600
agcgccgaca tgtctcatt aaccggtgcg gtaagcctcg catcaatgct gacggagata    660
tttctcctgc aacaagcaca gggaatgccg gagccgggt ggggaaggat caccgattca    720
caccagtgga cacccttgct aagtttgcat aacgcgcaat tttatttgct acaacgcacg    780
ccagaggttg cccgcagccg cgccaccccg ttattagatt tgatcaagac agcgttgacg    840
ccccatccac cgcaaaaaca ggcgtatggt gtgacattac ccacttcagt gctgtttatc    900
gccggacacg atactaatct ggcaaatctc ggcggcgcac tggagctcaa ctggacgctt    960
cccggtcagc cggataacac gccgccaggt ggtgaactgg tgtttgaacg ctggcgtcgg   1020
ctaagcgata acagccagtg gattcaggtt cgctggtct tccagacttt acagcagatg   1080
cgtgataaaa cgccgctgtc attaaatacg ccgcccggag aggtgaaact gaccctggca   1140
ggatgtgaag agcgaaatgc gcagggcatg tgttcgttgg caggttttac gcaaatcgtg   1200
```
aatgaagcac gcataccggc gtgcagtttg taa                      1233

<210> SEQ ID NO 3
<211> LENGTH: 410
<212> TYPE: PRT
<213> ORGANISM: Artifical sequence
<220> FEATURE:
<223> OTHER INFORMATION: phytase mutant APPA-M

<400> SEQUENCE: 3

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
```

```
                355                 360                 365
Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 1233
<212> TYPE: DNA
<213> ORGANISM: Artifical sequence
<220> FEATURE:
<223> OTHER INFORMATION: sequence encoding phytase mutant APPA-M

<400> SEQUENCE: 4
cagtcagaac cagagttgaa gttggagtca gtcgtcatcg ttagtagaca tggagttaga      60 gccccctacaa agtttaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa agtgtggttg ccctcaatct    240
ggacaggttg caattatcgc tgatgttgat gaaagaacta gaaaaacagg agaggctttt    300
gctgccggat tggccccaga ttgtgcaatc actgttcatc accaagccga tacatcttcc    360
ccagaccctt tgttcaaccc tcttaagaca ggagtctgtc agttggatgt tgccaatgtc    420
accagagcaa ttttggaaag agctggtgga agtatcgccg actttactgg tcactaccaa    480
acagctttca gagaattgga gagagttctt aactttccac agtccaattt gtgtcttaag    540
agagaaaagc aagatgagtc atgcagtttg actcaggctc ttccttctga gttgaaagtt    600
tccgccgaca acgtctcatt gaccggagct gttttctctt gcctccatgt tgactgaaatt    660 ttcttgcttc aacaggctca gggtatgcca gagcctggtt ggggaagaat caccgatagt    720
catcagtgga acactttgct ttcttttgcac aatgctcaat tcgacttgct tcagagaact    780
ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt ggagcttaa ctggacattg     960 ccaggtcaac tgataatac cccacctggt ggagaattgg ttttttgagag atggagaaga  1020 ttgtcagaca atagtcaatg gattcaggtt tccttggtct tccaaacttt gcaacagatg   1080
agagataaga caccattgtc acttaacacc ccacctggtg aagtcaaatt gacacttgcc   1140
ggatgtgaag agagaaatgc acaaggaatg tgcagtcttg ctggtttcac ccaaatcgtc   1200
aatgaggcta gaatccctgc ttgttccttg taa                                1233

<210> SEQ ID NO 5
<211> LENGTH: 410
<212> TYPE: PRT
<213> ORGANISM: Artifical sequence
<220> FEATURE:
<223> OTHER INFORMATION: phytase mutant PHY1

<400> SEQUENCE: 5

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30
```

Thr Pro Asp Ala Trp Pro Thr Trp Pro Val Lys Leu Gly Glu Leu Thr
 35                  40                  45

Pro Arg Gly Gly Glu Leu Ile Ala Tyr Leu Gly His Tyr Trp Arg Gln
 50                  55                  60

Arg Leu Val Ala Asp Glu Leu Leu Pro Lys Cys Gly Cys Pro Gln Ser
 65                  70                  75                  80

Gly Gln Val Ala Ile Ile Ala Asp Val Asp Glu Arg Thr Arg Lys Thr
                 85                  90                  95

Gly Glu Ala Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
                115                 120                 125

Lys Thr Gly Val Cys Gln Leu Asp Val Ala Asn Val Thr Arg Ala Ile
130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
                275                 280                 285

Tyr Gly Val Thr Leu Pro Thr Ser Val Leu Phe Ile Ala Gly His Asp
290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Pro Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 6
<211> LENGTH: 1233
<212> TYPE: DNA
<213> ORGANISM: Artifical sequence
<220> FEATURE:
<223> OTHER INFORMATION: sequence encoding phytase mutant PHY1

<400> SEQUENCE: 6

```
cagtcagaac cagagttgaa gttggagtca gtcgtcatcg ttagtagaca tggagttaga      60
gccccctacaa agtttaccca gcttatgcaa gatgttaccc cagacgcttg ccaacttgg     120
cctgtcaagt tgggagaact tactcctaga ggtggagagt tgattgccta ccttggtcat    180
tattggagac aaagattggt tgcagatgaa ttgcttccaa agtgtggttg ccctcaatct    240
ggacaggttg caattatcgc tgatgttgat gaaagaacta gaaaaacagg agaggctttt    300
gctgccggat tggccccaga ttgtgcaatc actgttcatc accaagccga tacatcttcc    360
ccagacccct tgttcaaccc tcttaagaca ggagtctgtc agttggatgt tgccaatgtc    420
accagagcaa ttttggaaag agctggtgga agtatcgccg actttactgg tcactaccaa    480
actgctttca gagaattgga gagagttctt aactttccac agtccaactt gtgtcttaag    540
agagaaaagc aagatgagtc ttgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga acacttttgct ttctttgcac aatgctcaat cgacttgct tcagagaact    780
ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt tggagcttaa ctggacattg    960
ccaggtcaac tgataatac cccacctggt ggagaattgg tttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttcct   1140
ggatgtgaag agagaaatgc acaaggaatg tgcagtcttg ctggtttcac ccaaatcgtc   1200
aatgaggcta gaatccctgc ttgttccttg taa                                 1233
```

<210> SEQ ID NO 7
<211> LENGTH: 410
<212> TYPE: PRT
<213> ORGANISM: Artifical sequence
<220> FEATURE:
<223> OTHER INFORMATION: phytase mutant PHY4

<400> SEQUENCE: 7

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125
```

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Pro Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 8
<211> LENGTH: 1233
<212> TYPE: DNA
<213> ORGANISM: Artifical sequence
<220> FEATURE:
<223> OTHER INFORMATION: sequence encoding phytase mutant PHY4

<400> SEQUENCE: 8
cagtcagaac cagagttgaa gttggagtca gtcgtcatcg ttagtagaca tggagttaga      60 gccccctacaa agtttaccca gcttatgcaa gatgttaccc cagacgcttg gccaacttgg    120
cctgtcaagt tgggagaact tactcctaga ggtggagagt tgattgccta ccttggtcat    180
tattggagac aaagattggt tgcagatgaa ttgcttccaa gtgtggttg ccctcaacca     240 ggacaggttg caattatcgc tgatgttgat gaaagaacta gaaaaacagg agaggctttt    300
gctgccggat ggcccccaga ttgtgcaatc actgttcatc accagccga tacatcttcc    360 ccagacccctt tgttcaaccc tcttaagaca ggagtctgtc agttggatgt tgccaatgtc   420
accagagcaa ttttggaaag agctggtgga agtatcgccg actttactgg tcactaccaa    480

```
actgctttca gagaattgga gagagttctt aactttccac agtccccatt gtgtcttaag    540
agagaaaagc aagatgagcc atgcagtttg actcaggctc ttccttctga gttgaaagtt    600
tccgccgaca acgtctcatt gaccggagct gtttctcttg cctccatgtt gactgaaatt    660
ttcttgcttc aacaggctca gggtatgcca gagcctggtt ggggaagaat caccgatagt    720
catcagtgga cactttgct ttctttgcac aatgctcaat cgacttgct tcagagaact    780 ccagaagttg caagatccag agctacacct ttgcttgatc ttattaagac cgcattgact    840
ccacatccac ctcaaaaaca ggcttatgga gttacattgc ctacctctgt cttgttcatc    900
gctggtcacg acactaactt ggcaaatctt ggtggagctt ggagcttaa ctggacattg    960 ccaggtcaac ctgataatac cccacctggt ggagaattgg tttttgagag atggagaaga   1020
ttgtcagaca atagtcaatg gattcaggtt tccttggtct tccaaacttt gcaacagatg   1080
agagataaga caccattgtc acttaacacc ccacctggtg aagtcaaatt gacacttcct   1140
ggatgtgaag agaaaatgc acaaggaatg tgcagtcttg ctggtttcac ccaaatcgtc   1200
aatgaggcta gaatccctgc ttgttccttg taa                                1233
```

<210> SEQ ID NO 9
<211> LENGTH: 410
<212> TYPE: PRT
<213> ORGANISM: Artifical sequence
<220> FEATURE:
<223> OTHER INFORMATION: phytase mutant PHY5

<400> SEQUENCE: 9

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Glu Leu Pro Lys Cys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Pro Ala Phe Arg Glu Leu Glu Arg Val Leu Asn Phe Pro Gln Ser Pro
                165                 170                 175

Leu Cys Leu Lys Arg Glu Lys Gln Asp Glu Pro Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220
```

| | | | | | | | | | | | | | | |
|---|---|---|---|---|---|---|---|---|---|---|---|---|---|---|
|Gln|Ala|Gln|Gly|Met|Pro|Glu|Pro|Gly|Trp|Gly|Arg|Ile|Thr|Asp Ser|
|225| | | |230| | | |235| | | | |240| |

His Gln Trp Asn Thr Leu Leu Ser Leu His Asn Ala Gln Phe Asp Leu
                245                    250                   255

Leu Gln Arg Thr Pro Glu Val Ala Arg Ser Arg Ala Thr Pro Leu Leu
        260                    265                   270

Asp Leu Ile Lys Thr Ala Leu Thr Pro His Pro Pro Gln Lys Gln Ala
    275                    280                   285

Tyr Gly Val Thr Leu Pro Thr Ser Val Leu Phe Ile Ala Gly His Asp
        290                    295                300

Thr Asn Leu Ala Asn Leu Gly Gly Ala Leu Glu Leu Asn Trp Thr Leu
305                    310                    315              320

Pro Gly Gln Pro Asp Asn Thr Pro Pro Gly Gly Glu Leu Val Phe Glu
                325                    330                335

Arg Trp Arg Arg Leu Ser Asp Asn Ser Gln Trp Ile Gln Val Ser Leu
            340                345                350

Val Phe Gln Thr Leu Gln Gln Met Arg Asp Lys Thr Pro Leu Ser Leu
        355                    360                   365

Asn Thr Pro Pro Gly Glu Val Lys Leu Thr Leu Pro Gly Cys Glu Glu
370                    375                    380

Arg Asn Ala Gln Gly Met Cys Ser Leu Ala Gly Phe Thr Gln Ile Val
385                    390                    395              400

Asn Glu Ala Arg Ile Pro Ala Cys Ser Leu
        405                    410

<210> SEQ ID NO 10
<211> LENGTH: 1233
<212> TYPE: DNA
<213> ORGANISM: Artifical sequence
<220> FEATURE:
<223> OTHER INFORMATION: sequence encoding phytase mutant PHY5

<400> SEQUENCE: 10

```
cagtcagaac cagagttgaa gttggagtca gtcgtcatcg ttagtagaca tggagttaga    60
gccccctacaa agtttaccca gcttatgcaa gatgttaccc cagacgcttg gccaacttgg   120
cctgtcaagt tgggagaact tactcctaga ggtggagagt tgattgccta ccttggtcat   180
tattggagac aaagattggt tgcagatgaa ttgcttccaa agtgtggttg ccctcaacca   240
ggacaggttg caattatcgc tgatgttgat gaaagaacta gaaaaacagg agaggctttt   300
gctgccggat tggccccaga ttgtgcaatc actgttcatc accaagccga tacatcttcc   360
ccagaccctt tgttcaaccc tcttaagaca ggagtctgtc agttggatgt tgccaatgtc   420
accagagcaa ttttggaaag agctggtgga agtatcgccg actttactgg tcactaccaa   480
ccagctttca gagaattgga gagagttctt aactttccac agtccccatt gtgtcttaag   540
agagaaaagc aagatgagcc atgcagtttg actcaggctc ttccttctga gttgaaagtt   600
tccgccgaca acgtctcatt gaccggagct gtttctcttg cctccatgtt gactgaaatt   660
ttcttgcttc aacaggctca gggtatgcca gagcctggtt ggggaagaat caccgatagt   720
catcagtgga cactttgct ttcttttgcac aatgctcaat tcgacttgct tcagagaact   780
ccagaagttg caagatccag agctacacct ttgcttgatc ttattaagac cgcattgact   840
ccacatccac tcaaaaaaca ggcttatgga gttacattgc ctacctctgt cttgttcatc   900
gctggtcacg acactaactt ggcaaatctt ggtggagctt tggagcttaa ctggacattg   960
ccaggtcaac ctgataatac cccacctggt ggagaattgg ttttgagag atggagaaga   1020
```

```
ttgtcagaca atagtcaatg gattcaggtt tccttggtct tccaaacttt gcaacagatg    1080
agagataaga caccattgtc acttaacacc ccacctggtg aagtcaaatt gacacttcct    1140
ggatgtgaag agagaaatgc acaaggaatg tgcagtcttg ctggtttcac ccaaatcgtc    1200
aatgaggcta gaatccctgc ttgttccttg taa                                 1233

<210> SEQ ID NO 11
<211> LENGTH: 32
<212> TYPE: DNA
<213> ORGANISM: Artifical sequence
<220> FEATURE:
<223> OTHER INFORMATION: primer XynII-F1

<400> SEQUENCE: 11
ggcgaattcc agtcagaacc agagttgaag tt                                    32

<210> SEQ ID NO 12
<211> LENGTH: 32
<212> TYPE: DNA
<213> ORGANISM: Artifical sequence
<220> FEATURE:
<223> OTHER INFORMATION: primer XynII-R1

<400> SEQUENCE: 12
atagcggccg cttacaagga acaagcaggg at                                    32
```

The invention claims:

1. A DNA molecule comprising a polynucleotide sequence encoding the phytase mutant comprising the amino acid sequence as set forth in SEQ ID NO: 3 or SEQ ID NO: 5 or SEQ ID NO: 7 or SEQ ID NO: 9.

2. The DNA molecule of claim 1, wherein the polynucleotide sequence is as set forth in SEQ ID NO: 4 or SEQ ID NO: 6 or SEQ ID NO: 8 or SEQ ID NO: 10.

3. An expression vector comprising the DNA molecule of claim 1.

4. A host cell comprising the expression vector of claim 3.

* * * * *